United States Patent
Michal

(10) Patent No.: US 7,678,143 B2
(45) Date of Patent: *Mar. 16, 2010

(54) ETHYLENE-CARBOXYL COPOLYMERS AS DRUG DELIVERY MATRICES

(75) Inventor: Gene Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 573 days.

This patent is subject to a terminal disclaimer.

(21) Appl. No.: 10/712,678

(22) Filed: Nov. 12, 2003

(65) Prior Publication Data

US 2004/0096504 A1 May 20, 2004

Related U.S. Application Data

(62) Division of application No. 09/748,719, filed on Dec. 22, 2000, now Pat. No. 6,824,559.

(51) Int. Cl.
*A61F 2/06* (2006.01)
(52) U.S. Cl. .................................... 623/1.46
(58) Field of Classification Search .............. 623/23.72, 623/23.73, 23.74, 23.75, 23.76, 23.6, 23.61, 623/23.62, 23.63, 23.51, 1.42, 1.15, 1.38–1.49; 424/484–487, 423
See application file for complete search history.

(56) References Cited

U.S. PATENT DOCUMENTS

| | | | | |
|---|---|---|---|---|
| 4,060,657 A | * | 11/1977 | Iwami et al. ............... 428/375 |
| 4,093,708 A | * | 6/1978 | Zaffaroni et al. ........... 424/427 |
| 4,142,526 A | * | 3/1979 | Zaffaroni et al. ........... 424/424 |
| 4,201,216 A | * | 5/1980 | Mattei ........................ 606/230 |
| 4,329,383 A | | 5/1982 | Joh ............................. 428/36 |
| 4,729,914 A | * | 3/1988 | Kliment et al. ............. 428/35.7 |
| 4,733,665 A | | 3/1988 | Palmaz ....................... 128/343 |
| 4,800,882 A | | 1/1989 | Gianturco ................... 128/343 |
| 4,882,168 A | | 11/1989 | Casey et al. ................. 424/468 |
| 4,886,062 A | | 12/1989 | Wiktor ....................... 128/343 |
| 4,941,870 A | | 7/1990 | Okada et al. ................ 600/36 |
| 4,977,901 A | | 12/1990 | Ofstead ...................... 128/772 |
| 5,112,457 A | | 5/1992 | Marchant ................... 204/165 |
| 5,165,919 A | | 11/1992 | Sasaki et al. ............... 424/488 |
| 5,272,012 A | | 12/1993 | Opolski ...................... 428/423.1 |

(Continued)

FOREIGN PATENT DOCUMENTS

EP 0 716 836 6/1986

(Continued)

OTHER PUBLICATIONS

Anonymous, *Cardiologists Draw—Up The Dream Stent*, Clinica 710:15 (Jun. 17, 1998), http://www.dialogweb.com/cgi/document?reg=1061848202959, printed Aug. 25, 2003 (2 pages).

(Continued)

*Primary Examiner*—Alvin J Stewart
(74) *Attorney, Agent, or Firm*—Squire, Sanders & Dempsey, L.L.P.

(57) ABSTRACT

A coated stent is provided including a coating composed of one or more co-polymers of ethylene with carboxylic acid wherein the carboxylic acid co-monomer content is 5-50 wt %.

8 Claims, 2 Drawing Sheets

U.S. PATENT DOCUMENTS

| | | | |
|---|---|---|---|
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,401,512 A * | 3/1995 | Rhodes et al. | 424/458 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,519,228 A * | 5/1996 | Takasu et al. | 250/484.4 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,631,328 A * | 5/1997 | Wang et al. | 525/329.7 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,866,266 A * | 2/1999 | Takasu | 428/690 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,948,529 A * | 9/1999 | Hastie | 428/373 |
| 5,955,509 A | 9/1999 | Webber et al. | 514/772.7 |
| 5,971,954 A | 10/1999 | Conway et al. | 604/98 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,087,412 A * | 7/2000 | Chabrecek et al. | 522/35 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,197,013 B1 | 3/2001 | Reed et al. | 604/509 |
| 6,200,337 B1 | 3/2001 | Moriuchi et al. | 623/1.16 |
| 6,203,551 B1 | 3/2001 | Wu | 606/108 |
| 6,206,916 B1 | 3/2001 | Furst | 623/1.46 |
| 6,231,600 B1 | 5/2001 | Zhong | 623/1.42 |
| 6,240,616 B1 | 6/2001 | Yan | 29/572.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,379 B1 * | 4/2002 | Wang | 623/1.15 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/145 |
| 6,585,926 B1 | 7/2003 | Mirzaee | 260/400 |
| 6,605,154 B1 | 8/2003 | Villareal | 118/500 |
| 6,656,601 B1 * | 12/2003 | Kawachi et al. | 428/483 |
| 6,824,559 B2 * | 11/2004 | Michal | 623/1.15 |
| 7,297,348 B2 * | 11/2007 | Li et al. | 424/485 |
| 2001/0009662 A1 * | 7/2001 | Cohn et al. | 424/78.17 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2004/0158194 A1 * | 8/2004 | Wolff et al. | 604/66 |

FOREIGN PATENT DOCUMENTS

| | | |
|---|---|---|
| EP | 0 301 856 | 2/1989 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 809 999 | 12/1997 |
| EP | 0 832 655 | 4/1998 |
| EP | 0 850 651 | 7/1998 |
| EP | 0 879 595 | 11/1998 |

| | | |
|---|---|---|
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996) http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Loss Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

ETHYLENE-CARBOXYL COPOLYMERS AS DRUG DELIVERY MATRICES

CROSS REFERENCE

This is a divisional of U.S. patent application Ser. No. 09/748,719 filed Dec. 22, 2000, which issued on Nov. 30, 2004 as U.S. Pat. No. 6,824,559.

BACKGROUND OF THE INVENTION

The present invention relates to a drug delivery matrix coating, to an implantable device comprising the drug delivery matrix coating, to a method for making the drug delivery matrix coating and to a method for applying the drug delivery matrix coating to a stent.

Stents are typically implanted within a vessel in a contracted state and expanded when in place in the vessel in order to maintain patency of the vessel to allow fluid flow through the vessel. Typically, implantation of such stents is accomplished by mounting the stent on the balloon portion of a catheter, positioning the stent in a body lumen, and expanding the stent to an expanded state by inflation of a balloon within the stent. The stent can then be left in place by deflating the balloon and removing the catheter.

Because of the mechanical strength that is required to properly support vessel walls, stents are typically constructed of metallic materials. However, it is frequently desirable to provide localized pharmacological treatment of a vessel at the site being supported by the stent. It is convenient to employ the stent as a vehicle for drug delivery. The metallic materials are not capable of carrying and releasing drugs. Polymeric materials capable of absorbing and releasing drugs typically do not fulfill the structural and mechanical requirements of a stent, especially when the polymeric materials are loaded with a drug, since drug loading of a polymeric material diminishes the structural and mechanical properties of the polymeric material. Since it is often useful to provide localized therapeutic pharmacological treatment of a vessel at the location being treated with the stent, it is desirable to combine such polymeric materials with existing stent structures to provide a stent with the capability of absorbing therapeutic drugs or other agents, for placement and release of the therapeutic agents at a specific intravascular site.

One solution historically used has been coating a stent's metallic structure with a polymeric material in order to provide a stent capable of both supporting adequate mechanical loads as well as delivering drugs. Techniques typically used to join polymers to metallic stents include dipping, spraying and conforming processes. However, these techniques have tended to introduce other problems into the stent products. Other problems with drug delivery matrix coatings include marginal adhesion to a substrate such as a metal substrate, insufficient elongation of the coating resulting in cracks, and limited and sub-optimal solvent choices that result in difficult application of the coating and poor manufacturability.

SUMMARY OF THE INVENTION

The present invention relates to a copolymer of carboxylic acid in a layer as applied in a drug releasing implant. The carboxylic acid copolymer may be in a matrix having a drug or in a primer or in a diffusion barrier.

One embodiment of the present invention includes a drug delivery coating. The drug delivery coating comprises a matrix comprising one or more co-polymers of ethylene comprising the reaction products of carboxylic acid containing unsaturated monomers. The drug delivery coating also includes a drug contacting the matrix. The drug delivery coating has a strong adhesion due to Van der Waals interaction resulting from carboxylic acid bonding of the coating to the material being coated.

One other embodiment of the present invention includes a stent. The stent comprises a tubular main body. The stent also comprises a coating that is adhered to the tubular main body. The coating comprises one or more co-polymers of ethylene wherein the co-polymers include a carboxylic acid moiety. The carboxylic acid moiety comprises one or more of acrylic acid, methacrylic acid, maleic acid, itaconic acid and all combinations and esters of these monomers. The coating deforms to a degree that accommodates stent deformation and, as a result, is resistant to cracking and delamination. The coating adheres to stents comprised of materials such as stainless steel.

Another embodiment of the present invention includes a drug delivery system. The drug delivery system comprises a tubular main body and a first coating that overlays the tubular main body. A drug is incorporated into the first coating. A coating comprising one or more co-polymers of ethylene with a carboxylic acid moiety overlays the first coating. The carboxylic acid moiety is one or more of acrylic acid, methacrylic acid, maleic acid, itaconic acid and all combinations and esters of these monomers. For some embodiments, the first coating is biodegradable.

Another embodiment of the present invention includes a method for improving manufacturability of a drug delivery system used with a medical device. The method comprises providing a medical device with a main body and providing a coating comprising a cross-linkable co-polymers of ethylene with carboxylic acid. The method also includes applying the coating to the main body of the medical device.

The drug delivery coating of the present invention adheres to a metal substrate and has an elongation comparable to a metal or polymeric substrate. The drug delivery coating is soluble in a ternary blend. The ternary blend eases application of the coating to a medical device surface, such as a stent. The ternary blend also improves manufacturability as compared to polymeric drug delivery systems not using the ternary blend.

DETAILED DESCRIPTION

Figure 1:
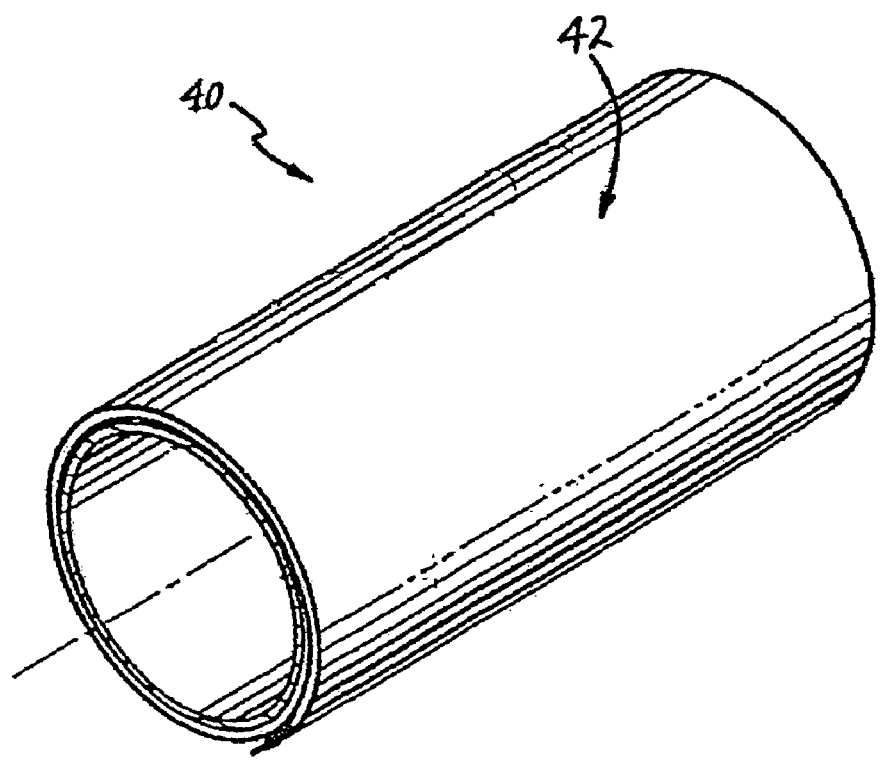
FIG. 1 illustrates a perspective view of one embodiment of the stent of the present invention.

One embodiment of the present invention comprises an array of matrix drug delivery coating 42 usable as drug delivery coatings for stents 40, namely metal stents and polymeric stents, such as are illustrated, in one embodiment, in FIG. 1. While a roll is shown in FIG. 1, it is understood that the coating may be a sheath or a thin coat for other implant embodiments. The array of matrix coatings comprises one or more cross-linkable co-polymers of ethylene comonomer, —($C_2H_4$)— that comprises one or more carboxylic acid moieties. The carboxylic acid moieties are, for some embodiments, unsaturated carboxylic acid monomers or unsaturated carboxylic acid co-monomers. The unsaturated carboxylic acid monomers or unsaturated carboxylic acid co-monomers are one or more of acrylic acid, methacrylic acid, maleic acid, itaconic acid and all combinations and esters of these monomers.

The carboxylic acid co-monomer content is at least about 5% by weight and not more than about 50% by weight of the polymer. The carboxylic co-monomer content is, for some embodiments, in a range of about 15 to 40% by weight of the polymer. The acid groups are, for some embodiments, partially neutralized. For other embodiments, the acid groups are fully neutralized using sodium hydroxide, potassium hydroxide, ammonia, and the like.

The term "ionomers" as used herein refers to polymers with acid groups that are neutralized with metal cations.

The term "matrix polymer" as used herein refers to a polymer capable of forming a coating on a surface of a medical apparatus and providing a network for containing a drug. The matrix polymer has functional moieties capable of crosslinking by hydrogen bonds to other moieties within the matrix polymer and crosslinking to any other moieties derived from the medical apparatus to enhance the strength and toughness of the coating. Adhesion is enhanced by Van der Waals interaction resulting from carboxylic acid bonding of the coating to the medical apparatus.

The term "elongation" as used herein refers to a percent elongation to break or an amount of strain the polymer can endure before rupturing.

Figure 2:
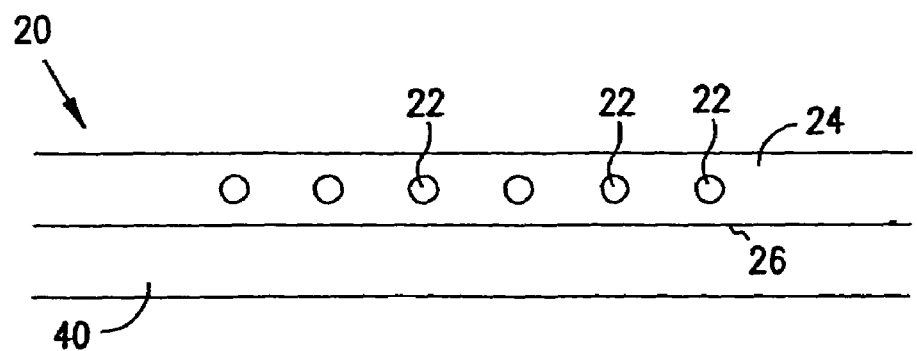
FIG. 2 illustrates a cross-sectional view of one embodiment of the drug delivery matrix of the present invention, wherein a drug is positioned within a polymeric matrix.

Another embodiment of the present invention includes the matrix drug delivery coating of the present invention and a drug. For some embodiments, such as is illustrated at 20 in FIG. 2, the polymer comprising the coating acts as a drug eluting matrix. The drug 22 is incorporated within the drug eluting matrix 24. For some embodiments, the drug is a particulate which is dispersed within the drug eluting matrix 24. For other embodiments, the drug is dissolved within the matrix 24.

The drug delivery coating acts as a barrier to rapid diffusion of the drug through the coating and to a treatment site. The drug delivery coating has a thickness ranging from about 0.1 to 3.0 mils, when applied to a stent. Because diffusion and drug release are delayed by the coating, the coating is usable for releasing drugs to a treatment site after a time interval of no or negligible drug release.

The coating of the present invention is usable with multiple drug delivery matrices in order to orchestrate drug release. In one embodiment, the coating, as shown in cross-section in FIG. 2, overlays a surface 26, such as a stent surface. With this embodiment, the coating functions as a drug release coating. For another embodiment which is not shown, the coating is drug free and does not function as a drug release coating.

For some embodiments, the coating made with co-polymers of ethylene is a primer layer or a diffusion barrier. As a primer layer, the coating adheres to the surface of a stent. The primer layer also has functional moieties for crosslinking to a matrix polymer. For some embodiments, the primer layer is a dispersion of ethylene acrylic acid (EAA), such as Primacor 5980, available from Dow-Corning Corp. in Midland, Mich. or MICHEMPRIME 4983R, available from Michelman of Cincinnati, Ohio, or which is a dispersion that is capable of providing carboxyl moieties to the surface. As a primer layer, the coating of the present invention deforms to a degree that accommodates stent deformation, such as stent strut deformation. As a result, the coating is resistant to cracking and delamination and provides both elongation and high adhesion. For some embodiments, a drug is incorporated in the primer or the diffusion barrier. Typically, the drug concentration for these embodiments is lower if the matrix layer is present.

Thus, the coating of the present invention accomplishes what many other polymers cannot perform. Thermosets such as epoxies, polyesters, phenolics, polyimide, as well as conventional thermoplastics such as vinyl chloride, cellulosics, styrene, methyl methacrylate and thermoplastics such as PEEK, PPS, polysulfone, polycarbonate, Mylar, unless the strain occurs above the polymer's glass transition temperature, do not elongate and adhere to a degree that makes them acceptable coatings for stent devices.

Figure 3A:
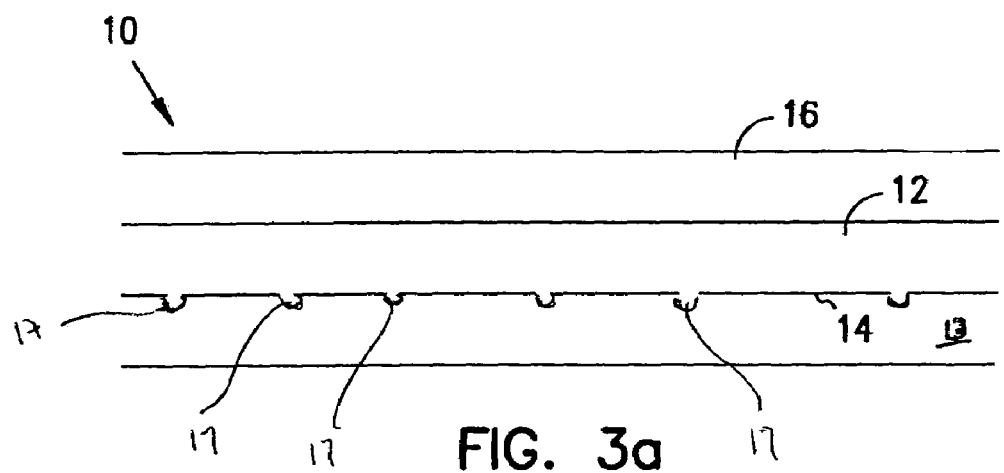
FIG. 3a illustrates a cross-sectional view of another embodiment of the drug delivery matrix of the present invention wherein a polymeric matrix overlays a drug-containing matrix.

For other embodiments, the polymer comprising the coating is positioned to provide a diffusion limiting barrier for a drug reservoir, such as a micro-depot 17, shown in FIG. 3a. The micro-depot 17 is defined by a divot formed at the surface 14 of the stent 13. This embodiment is illustrated generally at 10 in FIG. 3a. A coating illustrated at 12 overlays a stent surface 14. For some embodiments, the coating 12 includes drugs and for other embodiments, the coating 12 is drug-free. The polymer overcoat 16 of the present invention overlays the coating 12. The coating matrix includes one or more of poly (ethylene-acrylic acid), EAA, poly(ethylene-vinyl alcohol), poly(ethylene vinyl acetate), poly n-butyl methacrylate, poly (ethylene oxide) or a polyurethane elastomer such as Bionate 80A, manufactured by Polymer Technology Group of Berkeley, Calif. Bionate 80 is a polycarbonate-urethane and is a thermoplastic elastomer formed as a reaction product of a hydroxyl terminated polycarbonate, an aromatic diisocyanate, and a low molecular weight glycol which is used as a chain extender. The overcoat 16 includes one or more of EAA, ethylene-methacrylic acid (EMAA), and other ethylene, acrylic acid-based materials.

Figure 3B:
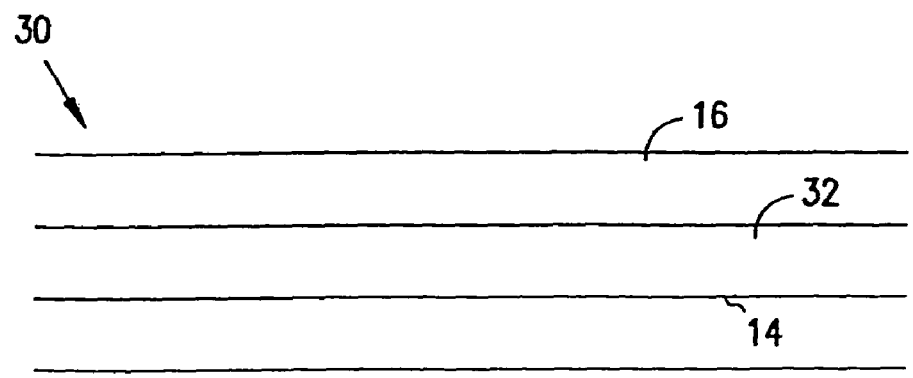
FIG. 3b illustrates a cross-sectional view of another embodiment of the drug delivery matrix of the present invention wherein the polymeric matrix overlays the drug-containing matrix.

For other embodiments such as is illustrated at 30 in FIG. 3b, the polymer overcoat 16 functions as a cover over a drug-only layer 32 or a drug/non-drug mixture layer, which is not shown. The coat may be biodegradable but there may be non-biodegradable coats, as well. One layer of this type is a layer that comprises a drug and a biodegradable material such as phosphatidylcholine. Other suitable biodegradable materials include linear aliphatic polyesters like polyglycolide and polylactide from poly(alpha-hydroxyacetic acids), poly (orthoesters), polyanhydrides, polysaccharides, poly(ester amides), tyrosine-based polyarylates or polyiminocarbonates or polycarbonates, poly(D,L-lactide-urethane), poly(beta-hydroxybutyrate), poly(e-caprolactone), poly[bis(carboxylatophenoxy) phosphazene], poly(amino acids), pseudo-poly (amino acids), and copolymers derived from amino acids and non-amino acids. As the biodegradable layer degrades, the drug is released.

For other embodiments, the matrix polymer coats a medical device such as a stent as shown at 40 in FIG. 1 but the polymer acts as a primer, and is free of drugs. For these embodiments, the matrix polymer 42 coats surfaces that are regarded as difficult to coat, such as stainless steel. Stainless steel is regarded as a difficult to coat metal because stainless steel has an outer surface that is trivalent chromium oxide, which provides a less reactive surface than other metal oxides. It is the interactions between metal oxides on the substrate and functional groups on the polymer that provide the adhesive force.

For some embodiments, the polymer coating formulation of the present invention also includes one or more of a surfactant, a colorant, and one or more plasticizers or mixtures of these materials. Some of the co-polymer coating embodiments of the present invention comprise co-polymers that are soluble in ternary blends comprising toluene, a chlorinated solvent, and a lower alcohol. The ternary blends of toluene, chlorinated solvents, and lower alcohols, are usable to dissolve and to apply the polymer or polymer/drug blend to a stent. For example, a blend of 15% trichloroethane, 15% 2-propanol and 70% toluene is usable to dissolve a coating polymer manufactured by Dow Chemical, PRIMACOR 5980. For some embodiments, the polymer coating formulation is dissolved at an elevated temperature. The use of these ternary blends renders the coating application process easier in that a coating has a viscosity that eases application and uniformity of thickness.

Specifically, solvents dissolve the polymer to make a coating solution. Surfactants are added to improve substrate wetting. Surfactants are also added to prevent foaming. Plasticizers increase elongation at the expense of hardness and tensile strength.

The co-polymers are neutralized in a volatile or a nonvolatile base. The copolymers are dispersed in water and in co-solvents such as the ternary blends that are described. Specifically, the co-solvents include the ternary blends of toluene, chlorinated solvents and lower alcohols.

In one particular example, a coating of the present invention is made with a PRIMACOR 5980I, which is manufactured by Dow Chemical of Midland, Mich. The PRIMACOR 5980I is an ethylene acrylic acid copolymer, EAA, that adheres to metals and other polar substrates. The PRIMACOR 5980I has the physical properties described in Table 1.

TABLE 1

| Physical Properties | Test Method | Values (SI) |
| --- | --- | --- |
| Resin Properties | | |
| Weight Percent Comonomer | Dow Method | 20.5 |
| Melt Index, g/10 min | ASTM D 1238 | 300 |
| Melt Flow Rate, g/10 min | ASTM D 1238 | 13.8 |
| Density, g/cc | ASTM D 792 | 0.958 |
| DSC Melting Point, F. (C.) | Dow Method | 171 (77) |
| Vicat Softening Point, F. (C.) | ASTM D 1525 | 108 (42) |
| Molded Part Properties | | |
| Ultimate Tensile, psi (Mpa) | ASTM D 638 | 1400 (10) |
| Ultimate Elongation, % | ASTM D 638 | 390 |
| Tensile Modulus, 2% secant, psi(MPa) | ASTM D 638 | 4800 (33) |
| Hardness, Shore D | ASTM D 2240 | 50 |

One other polymer formulation usable in the coating formulation of the present invention is provided in an ammonia neutralized aqueous dispersion at 25% solids, manufactured by Michelman Inc. The product name is Michem Prime 4983R. The Michem Prime 4983R product includes EAA solids in a percent of 25% non-volatiles. Dow Primacor 5980i is also usable. The specific gravity is 0.98 to 1.00. The particle size is about 0.03 micron. The viscosity is about 50 to 400, as measured with a No. 2 spindle. The hardness, as measured by ASTM test D-5, is about 54 sd.

This Michem Prime 4983R dispersion is, for some embodiments, blended in a concentration that is less than 40% w/w, and is preferably within a range of 5 to 20% w/w with a co-solvent and, optionally, with a drug component. This dispersion is applied by standard coating application techniques such as spray coating or dipping, at substantially room temperature. When used as a primer, an addition of about 20 to 50 micrograms of coating material per stent is typically used. As a matrix with drug, about 50 to 500 micrograms per stent are applied to each stent. If used as a diffusion limiting barrier coat, a quantity of about 50 to 500 micrograms of material are applied to each stent. Once the coating is applied to a stent, the coating and stent are baked at low temperature, 120 degrees to 150 degrees F., for a period of time that is sufficient to drive off the solvents and any volatile amine. Coating and heating produces a conformal coating on the device. For some embodiments, the coating is dried at room temperature, rather than being subjected to baking.

Another embodiment of the present invention includes a stent or other implantable medical device made with the coating of the present invention. The medical device comprises a main body comprising a material such as stainless steel, nickel, gold, chrome, nickel titanium alloy, platinum, other metals, silicone, polyethylene, other polyolefins, polyesters, other plastics, glass, polyurethane, acetal, polyamide, and polyvinyl chloride. Medical devices include catheters, microcatheters, wires, wound drains and dressings, arteriovenous shunts, gastroenteric tubes, urethral inserts, laparoscopic equipment, pellets and implants. The medical devices are made for some embodiments with coating alone. For other embodiments, the medical devices deliver drugs through the drug delivery coating.

The drug delivery coating of the present invention substantially eliminates problems of marginal substrate adhesion, insufficient elongation resulting in cracks and limited and sub-optimal solvent choices resulting in difficult application and poor manufacturability. The carboxylic acid groups of the ethylene polymer impart a high adhesion to the coating so that the coating strongly adheres to metal. The ethylene content insures sufficient elongation of the coating to accommodate the strain associated with stent expansion.

An ability to neutralize the acid groups with a volatile or permanent counter ion provides water dispersibility properties to the coating. The water dispersibility is compatible with organic co-solvents such as 2-propanol or methyl ethyl ketone to aid in substrate wetting and improved application properties. The acid groups that are not ionically neutralized in the dried film are usable to associate with amine groups on a drug, such as Actinomycin D, and to retard its release.

Thus, the drug delivery coating of the present invention resists wet abrasion. The coating remains coherent without cracks despite flexing when applied to substantially inert surfaces that are difficult to coat, such as stainless steel. This performance is an improvement over other coatings which do not display optimal properties when applied to stainless steel.

Due to a high ethylene content, the hydrophobic nature of the dry film retards the transport of drug molecules, which tend to be functionalized and have some hydrophilic character.

Examples of such active ingredients include antiproliferative substances as well as antineoplastic, anti-inflammatory, antiplatelet, anticoagulant, antifibrin, antithrombin, antimitotic, antibiotic, antioxidant, and combinations thereof. A suitable example of an antiproliferative substance includes actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include actinomycin, actinomycin IV, actinomycin I1, actinomycin X1, and actinomycin C1. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin; vapiprost, prostacyclin arid prostacyclin analogs, dextran, D-phe-pro-arg-chloro-methylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

While the foregoing therapeutic agents have been used to prevent or treat restenosis, the drugs are provided by way of example and are not meant to be limiting, since other therapeutic drugs may be developed which are equally applicable for use in the present invention. The treatment of diseases using the therapeutic agents described as well as dosage rates are known.

For some embodiments, a selected drug is intimately mixed with the polymeric coating material of the present invention in order to uniformly disperse the therapeutic drug in the polymeric material. For other embodiments, the drug is incorporated into a matrix such as a biodegradable polymer matrix. The specific method of uniformly dispersing the therapeutic drug in the polymer is variable, and depends upon the stability of the therapeutic drug to thermal processing. Ethylene and acrylic acid, for example, are co-polymerized by free radical techniques to form an essentially linear polymer. However, ethylene is not "crosslinked" by the acid co-polymer. The acid groups randomly placed along the chain hydrogen bond to each other. The acid groups crosslink each other, not the ethylene groups.

For some embodiments, the therapeutic drug is uniformly dispersed in the polymeric material by coextruding small solid particles of the drug with the polymer material. The specific method of uniformly dispersing the therapeutic drug in the polymer varies and depends upon the stability of the therapeutic drug to thermal processing. The therapeutic drug is uniformly dispersed in the polymeric material by coextruding small solid particles of the selected therapeutic drug with the selected polymeric material. This extrusion device includes a hopper into which the polymeric material and small particles of selected therapeutic drug are added together, and into which a porosigen is also added, if desired. The extruder also typically includes a lead screw that drives and that intimately mixes the ingredients together, to uniformly disperse the small particles of the therapeutic drug, and if desired, a porosigen as well, in the polymeric material.

The barrel of the extruder is heated by temperature controlled heaters surrounding the barrel in stagers. A motor and associated gears are provided to drive the lead screw, and a cooling system is also typically provided. This method of intimately mixing the therapeutic drug and polymeric material yields a relatively high and uniformly distributed loading of the therapeutic drug in the polymer. While a loading of the therapeutic drug is currently no more than about 40% by weight, depending upon the specific application and interaction of the polymer with the drug, drug loadings as high as 70% by weight have been achieved by this method. A preferable concentration range is 5 to 20% by weight. The drug loaded polymer is extrudible into an appropriate shape, or can be subsequently calendered to produce a drug loaded polymer film having a smooth surface, with the therapeutic drug uniformly distributed in the film.

A polycarbonate-urethane material such as Bionate 80 is very hygroscopic. Pellets of Bionate 80 are dried by a process, such as with a forced air dehumidifying dryer at 82 degrees C for at least about 4 hours prior to extrusion or injection molding. Bionate 80 pellets are typically filtered during extrusion through filters such as a 350 mesh filter and two 500 mesh filters.

Extrusion equipment is set with a cross head temperature of about 200 degrees C to 215 degrees C to initiate the flow. Once flow is established, the cross head temperature is decreased until steady, viscous flow is achieved. Extrusion conditions for the polycarbonate-urethane material are typically within the following ranges:

| Conditions | Temperature (C.) | Temperature (F.) |
|---|---|---|
| Barrel-Zone 1 | 200-215 | 390-420 |
| Barrel-Zone 2 | 193-230 | 380-445 |
| Barrel-Zone 3 | 193-230 | 380-445 |
| Die | 200-215 | 390-420 |
| Melt Temperature | 191-221 | 375-430 |
| Extruder Configuration | | |

| Parameter | Value |
|---|---|
| Length to Diameter Ratio | 24:1 |
| Compression Ratio | 2.5:1 to 3.5:1 |
| Cooling Water Temperature | 18-20 degrees C. |

The particles of the desired therapeutic drug are formed to have a maximum cross-sectional dimension of about 10 microns. An average particle size of less than 10 microns and a uniform distribution of the particles of the therapeutic drug in the polymeric material provide a therapeutically effective amount of the therapeutic drug in the layer of the polymeric material to be applied to the structure of the stent, since the layer of polymeric material typically is as thin as 25 microns. The size and distribution of the particles of the therapeutic drug affect the physical properties of the polymer.

In other embodiments, the therapeutic drug is compounded with the polymer by calendering the ingredients, such as in a two roll mill, for example. This method yields a relatively high and uniformly distributed loading of the therapeutic drug in the polymer.

The matrix coating is applicable to the surface of a stent using methods such as dipping, spraying, flowing, rolling and brushing. Thickness of the coating ranges from about 0.1 to about 3 mils. The thickness is adjustable by adjusting viscosity of the coating material prior to application. Thickness is also adjustable by applying multiple coating layers.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced, otherwise than as specifically described.

What is claimed is:

1. A method of coating an implantable medical device, comprising:
adding a copolymer of an ethylene comonomer with a carboxylic acid comonmer to a solvent system to form a composition;
mixing a therapeutic drug with the copolymer composition to allow the drug uniformly dispersed in the copolymer composition, wherein the drug concentration is 5% to 20% by weight;
applying the composition to an implantable medical device; and
allowing the solvent system to evaporate;
wherein the carboxylic acid comonomer content is 5%-50 wt %.

2. The method of claim 1, wherein the carboxylic acid comonomer is selected from a group consisting of acrylic acid, methacrylic acid, maleic acid, itaconic acid, and esters thereof.

3. The method of claim 1, wherein adding the copolymer to the solvent system further comprises neutralizing the copolymer in a volatile or a non-volatile base and dispersing the copolymer in water and/or a co-solvent.

4. The method of claim 1, wherein the solvent system comprises toluene.

5. The method of claim 4, wherein the solvent system further comprises a chlorinated solvent and a lower alcohol.

6. The method of claim 1, wherein the carboxylic acid co-monomer has a content in the copolymer 15% to 40% by weight.

7. The method of claim 1, wherein the co-polymer is ethylene acrylic acid.

8. The method of claim 1, wherein the device comprises a stent.

* * * * *